(12) United States Patent
Popescu et al.

(10) Patent No.: US 11,511,113 B2
(45) Date of Patent: Nov. 29, 2022

(54) AVOIDANCE OF PERIPHERAL NERVE STIMULATION (PNS) USING INDUCED ANALGESIA

(71) Applicants: Siemens Healthcare GmbH, Erlangen (DE); The General Hospital Corporation, Boston, MA (US)

(72) Inventors: Stefan Popescu, Erlangen (DE); Lawrence Wald, Cambridge, MA (US); Bruce Rosen, Lexington, MA (US); Jason Stockmann, Cambridge, MA (US)

(73) Assignees: Siemens Healthcare GmbH, Erlangen (DE); The General Hospital Corporation, Boston, MA (US)

( * ) Notice: Subject to any disclaimer, the term of this patent is extended or adjusted under 35 U.S.C. 154(b) by 699 days.

(21) Appl. No.: 16/543,064

(22) Filed: Aug. 16, 2019

(65) Prior Publication Data
US 2021/0046315 A1   Feb. 18, 2021

(51) Int. Cl.
| | |
|---|---|
| *A61B 5/05* | (2021.01) |
| *A61N 1/36* | (2006.01) |
| *A61B 5/055* | (2006.01) |
| *A61N 2/00* | (2006.01) |
| *A61N 1/05* | (2006.01) |
| *G01R 33/00* | (2006.01) |

(52) U.S. Cl.
CPC .......... *A61N 1/36071* (2013.01); *A61B 5/055* (2013.01); *A61N 1/36057* (2013.01); *A61N 2/008* (2013.01); *A61N 1/0551* (2013.01); *A61N 2/006* (2013.01); *G01R 33/0082* (2013.01)

(58) Field of Classification Search
CPC . A61N 2/06; A61N 2/02; A61N 2/002; A61N 2/006; A61N 2/008; A61B 5/055
See application file for complete search history.

(56) References Cited

U.S. PATENT DOCUMENTS

| | | | | |
|---|---|---|---|---|
| 5,592,085 A | * | 1/1997 | Ehman | A61B 5/0051 324/309 |
| 6,234,953 B1 | * | 5/2001 | Thomas | A61N 2/008 600/14 |
| 2009/0149895 A1 | * | 6/2009 | Dacey, Jr. | A61N 1/36167 607/3 |

FOREIGN PATENT DOCUMENTS

CN          101069769 A       11/2007

OTHER PUBLICATIONS

G. Gh. Litarczek, et al.: "Research in electro-acupuncture anaesthesia," in: 1st International Conference on Advancements of Medicine and Health Care through Technology, MediTech2007, Sep. 27-29, 2007, Cluj-Napoca, Romania.

* cited by examiner

*Primary Examiner* — Rajeev P Siripurapu
(74) *Attorney, Agent, or Firm* — Banner & Witcoff Ltd.

(57) ABSTRACT

Techniques are disclosed related to increasing prior limits imposed on MR gradient switching speed (dB/dt) without causing significant discomfort or severe pain perception to patients. The technique disclosed herein do so by modifying the pulsing gradient fields that are ordinarily available for MR imaging protocols. Doing so stimulates the peripheral nerves and thus enables a quick, reversible, and complete inhibition of action potential propagation through the stimulated region of tissue, referred to as a nerve conduction block.

18 Claims, 6 Drawing Sheets

AVOIDANCE OF PERIPHERAL NERVE STIMULATION (PNS) USING INDUCED ANALGESIA

TECHNICAL FIELD

The present disclosure concerns techniques of inducing localized analgesia and, in particular, to techniques used in accordance with magnetic resonance imaging (MRI) scanners to alleviate peripheral nerve stimulation (PNS) during MRI procedures.

BACKGROUND

Faraday's Law of Induction states that changing magnetic fields induce electrical currents in any conducting medium. Thus, in accordance with Faraday's Law, exposure of conductive tissue to time-varying magnetic fields used in MRI scanners induces an electric field and currents into a patient's body. Induced currents are proportional to the conductivity of the conducting medium and the rate of change of the magnetic field. Therefore, time-varying magnetic fields (e.g., the gradients in MRI) will induce circulating eddy currents in conductors in the body, and particularly in electrically excitable nerve and muscle cells. Sufficiently large gradient fields, therefore, may even affect normal cell function.

A well-established example of this is the sensation of flashes of light—magnetophosphenes—caused by induced electric currents stimulating the retina. A more serious consequence of electric currents flowing through the body is ventricular fibrillation (though these levels are strictly prevented in MRI). In MR, this induction effect is determined by factors such as pulse duration, wave shape, repetition pattern, and the distribution of current in the body, which changes with the patient's position, coil geometry, gradient axis, nerve type, and nerve trajectory. The faster the MR imaging sequence, the greater the rate of change of the gradients, and therefore the resultant current density induced in the tissue is higher. MRI techniques which employ fast gradient switching (e.g. echo-planar imaging, or "EPI") can induce PNS for patients, which may manifest itself as an uncomfortable, annoying, or even painful sensation in some cases.

SUMMARY

As noted above, MRI procedures may induce PNS in patients during scanning. The stimulation threshold is the smallest for peripheral nerve stimulation, higher for stimulation of the skeletal muscle, and it is the greatest for cardiac muscle. Research with dogs has shown that respiratory stimulation occurs at exposure levels of 3 times higher than is required for peripheral nerve stimulation, while cardiac stimulation occurs at exposure levels 80 times higher. The current densities achieved when operating standard MRI systems are well below these values. EPI, however, uses increased gradient amplitudes and faster rise times, and thus is more likely to cause PNS, although cardiac and respiratory functions are not at risk. Therefore, the current regulatory limits, which apply for the operation of the gradients in an MR scanner, rely on a practical rule. Specifically, a device is classified as subjecting patients to significant risk any time the rate of change of gradient fields (dB/dt) is sufficiently high to produce severe discomfort or painful nerve stimulation.

The Physiology of Perceiving Pain

The perception of pain is also subjective, however, further complicating the issue of applying a uniform standard. Moreover, it is known that different types of stimulation to afferent nerve fibers lead to different responses. Some intense stimuli may trigger reflex withdrawal, as well as certain autonomic responses that regulate bodily functions such as the heart rate, digestion, respiratory rate, pupillary response, and some others trigger the perception of pain. The specific receptors for these intense stimuli are referred to as nociceptors.

In mammals, nociceptors are found in any area of the body that can sense noxious stimuli capturing actual or potential tissue-damaging events. External nociceptors are found in tissue such as the skin (cutaneous nociceptors), the corneas, and the mucosa. Internal nociceptors are found in a variety of organs, such as the muscles, the joints, the bladder, the gut, and the digestive tract. The cell bodies of these neurons are located in either the dorsal root ganglia (also known as the spinal ganglion) or the trigeminal ganglia. The trigeminal ganglia are specialized nerves for the face, whereas the dorsal root ganglia are associated with the rest of the body. The axons extend into the peripheral nervous system and terminate in branches to form the so called "receptive fields."

The main somatosensitive pain input in the human body uses C fibers in the anterolateral spinothalamic tract. C fibers are one class of nerve fiber found in the nerves of the somatic sensory system. These are known as afferent fibers, conveying input signals from the periphery to the central nervous system. C fibers are unmyelinated, unlike most other fibers in the nervous system. This lack of myelination is the cause of their slow conduction velocity, which is on the order of no more than 2 m/s. C fibers are on average 0.2-1.5 μm in diameter.

Afferent nociceptive fibers (those that send information to, rather than from the brain) travel back to the spinal cord where they form synapses in its dorsal horn. This nociceptive fiber (located in the periphery) is a first order neuron. The cells in the dorsal horn are divided into physiologically-distinct layers called laminae. Different fiber types form synapses in different layers, and use either glutamate or substance P as a neurotransmitter. Aδ fibers form synapses in laminae I and V, C fibers connect with neurons in lamina II, and Aβ fibers connect with lamina I, III, & V. After reaching the specific lamina within the spinal cord, the first order nociceptive project to second order neurons that cross the midline at the anterior white commissure. The second order neurons then send their information via two pathways to the thalamus: the dorsal column medial-lemniscal system and the anterolateral system. The former is reserved more for regular non-painful sensation, while the latter is reserved for pain sensation. Upon reaching the thalamus, the information is processed in the ventral posterior nucleus and sent to the cerebral cortex in the brain via fibers in the posterior limb of the internal capsule.

The Physiology of Mitigating Pain

As there is an ascending pathway to the brain that initiates the conscious realization of pain, there also is a descending pathway which modulates the pain sensation. The brain can request the release of specific hormones or chemicals that can have analgesic effects, which can reduce or inhibit pain sensation. The area of the brain that stimulates the release of these hormones is the hypothalamus. Stimulation of the hypothalamus determines β-endophine secretion which through blood and liquor spreads to the central nervous system and other peripheral systems.

It has been speculated that the traffic through the C fibers could be suppressed by using electro-acupuncture. Doing so may "close the gate" at a metameric level via stimuli coming through collaterals from Aδ and Aβ inputs, which are produced by acupuncture high frequency stimulation as well as by inhibitory stimuli coming from brainstem periaqueductal gray nucleus and reticular nuclei when stimulated by low frequency. The periaqueductal gray nucleus is also known as the central gray, and is the primary control center for descending pain modulation. The periaqueductal gray nucleus has enkephalin-producing cells that suppress pain, and the periaqueductal grey also contains opioid receptors, which explains one of the mechanisms by which opioids such as morphine and diacetylmorphine exhibit an analgesic effect. The reticular formation is one means by which pain signals from the lower body reach the cerebral cortex. It is also the origin of the descending analgesic pathways. The nerve fibers in these pathways act in the spinal cord to block the transmission of some pain signals to the brain (pain modulation).

In the backdrop of this anatomical information regarding the mitigation of perceived pain via electrical stimulation, the embodiments as described herein aim to increase prior limits imposed on MR gradient switching speed (dB/dt) without causing significant discomfort or severe pain perception to patients. The embodiments as described herein make use of pulsing gradient fields as available for MR imaging protocols to stimulate the peripheral nerves and thus enable a quick, reversible, and complete inhibition of action potential propagation through the stimulated region of tissue, referred to as a nerve conduction block.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

The exemplary embodiments of the present disclosure will be described with reference to the accompanying drawings. The drawing in which an element first appears is typically indicated by the leftmost digit(s) in the corresponding reference number.

DETAILED DESCRIPTION

Currently, MRI gradient coils are designed to minimize PNS effects using basic rules and previously-recorded data generated from a history of known safe use. In particular, this history is obtained from scanner manufacturers who have conducting several tests with many volunteers with the goal of determining the stimulation limits inducing discomfort or pain in a healthy population of subjects. This data may then be used in clinical operation to set the operating point of MR scanners below these limits by some threshold amount. Therefore, current design techniques to avoid PNS require the time-consuming and arduous task of separately testing and validating each new gradient system.

While PNS during MRI scans is not necessarily considered an adverse health effect, it does cause patient discomfort, which may induce unconscious patient motion, and is often followed by more painful stimulation. Typically, PNS begins as a slight tingling sensation but may progress to a twitch sensation and, if these sensations become strong enough, PNS may become painful.

Current solutions to counter PNS effects may involve the use of analgesic drugs before and/or during an MRI, with the aim being to induce a "comfortable" general analgesia involving as many potential painful regions as possible. However, there are side effects associated with drugs—namely, nausea and vomiting. Other negative effects caused by systemic analgesics are drowsiness, respiratory depression, and lowering of blood pressure (hypotension). Furthermore, systemic analgesics unselectively eliminate or reduce different forms of sensation, i.e., these dull pain as well as other senses such as touch, temperature, etc., as these different forms of sensation stimulate an area of the body and travel to the spinal cord by different nerve fibers in the same nerve bundle. When sensory nerves reach the spinal cord, however, their fibers separate and follow different courses to the brain. Thus, it is possible for certain forms of sensation to be lost, while others are preserved, as is the case in diseases that affect only certain areas of the spinal cord. Moreover, because pain and temperature sensations often travel the same path, both may be lost together. But there are significant patient safety related risks associated with an overall loss of the patient's ability to detect temperature sensations during an MRI exam. Therefore, although the use of systemic analgesic drugs to reduce PNS effects is a low-cost and simple solution, their use presents significant disadvantages.

Other solutions to counter PNS effects during MRI scans include inducing analgesia over a larger area of the body without the use of whole body analgesia like the one induced by pain relief drugs. The aim is to provoke or stimulate comfortable analgesia by way of traditional acupuncture that involves as much of the expected painful territory as possible. Acupuncture is a form of alternative medicine and a key component of traditional Chinese medicine. It is most often used for pain relief by stimulating the acupuncture points associated with pain regions such as the back and neck, knee, to treat headaches, shoulder pain, etc.

Using these techniques, a parallel stimulation of the acupuncture points associated with the body region expected to be impaired by MR gradient activities may be applied during an MR scanning session. Although the most common mechanism of stimulation of acupuncture points employs penetration of the skin by thin metal needles, there are five main types of simulation that can be applied on acupoints or reflex zones of body surface including via mechanical, electrical, thermal, magnetic, and photic stimulation. Classical needling and acupressure are associated with mechanical stimulation. Moxibustion (the burning of herbs close to or on the surface of the skin) and infrared radiation are associated with thermal stimulation. With regards to magnetic stimulation, some magnetic pellets may be applied to a region that are made from permanent magnetic materials. Laser acupuncture pertains to the photic stimulations. Such solutions typically implement infrared light (e.g., via an LED source) to deliver thermal stimulation to particular patient regions as needed.

Figure 1:
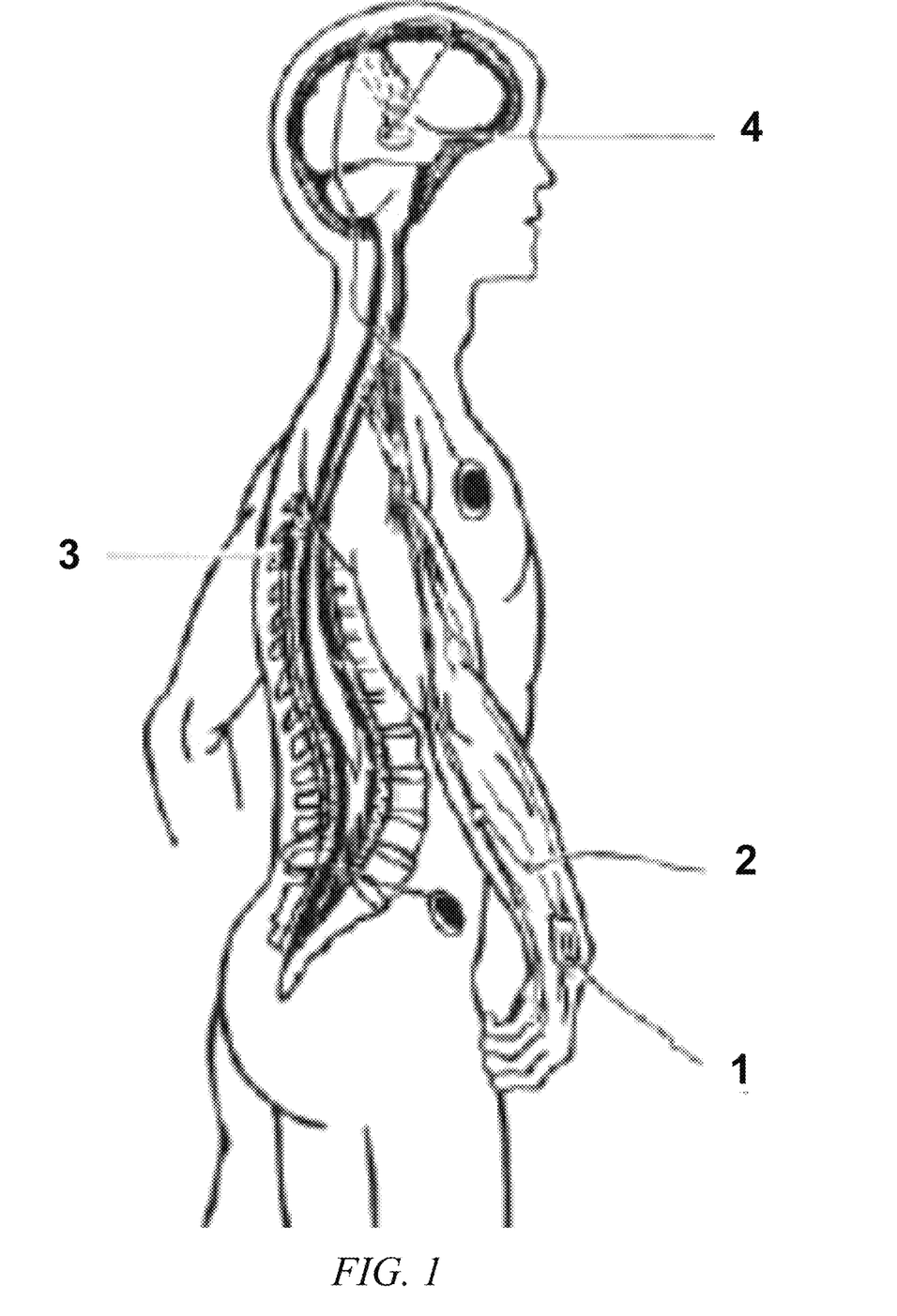
FIG. 1 illustrates the different sites at which conventional electrical neurostimulation is generally performed.

Other current approaches include the use of electrical stimulation for pain inhibition, which implement techniques that attempt to perform electrical stimulation of the human pain inhibition system. Such pain relieving effects have been achieved by stimulating directly at the level of nerve bundles (the first afferent sensory neuron), at the posterior horn of the spinal cord, or at the deep cerebral level (sensitive thalamic and periaqueductal nuclei). Generally, such electrical neurostimulation uses surface or implanted electrodes and wires, which is typically performed at four different sites as shown in FIG. 1. These include the skin via transcutaneous stimulation (1), the stimulation of peripheral nerves (2), the stimulation of spinal dorsal columns (3), and thalamic stimulation via sensory thalamic nuclei (4).

A variety of different stimulation therapies and techniques exist within the domain of electrical stimulation. For example, low frequency (<100 Hz) electrical stimulation is typically used to excite neuronal structures such as cell bodies, axons or ganglia, resulting in the generation of action potentials. Higher frequency (100 Hz-1 kHz) electrical stimulation is used to modulate deep brain structures, the spinal cord, and peripheral nerves. Depending on the particular structure that is stimulated, high frequency stimulation can lead to the generation of action potentials or to the depletion of neurotransmitters. Less understood and investigated, kilohertz (>1 kHz) electrical stimulation (KES) has increased in usage as a neuromodulation therapy in the last decade.

For example, reference [1] describes an electro-acupuncture verification trial study that found the most effective stimulation parameters to be 3 Hz (±2 Hz), 100 Hz (±10 Hz), and alternating between 2 Hz and 100 Hz. The low frequency excitation generates in the brain and spinal cord three of the species endogenous morphine: morphine, enkephalins, and endorphins, whereas the high frequency stimulation generates the endogenous morphine dynorphin. Alternating between two frequencies (2 Hz and 100 Hz) by way of compressional wave can thus simultaneously generate all 4 types of endogenous morphine. Human and animal experiments show that alternating two frequencies every 3 s±0.5 s seconds (the most in line with the requirements of endogenous morphine neurotransmitters half-life) will achieve the best results.

Figure 2:
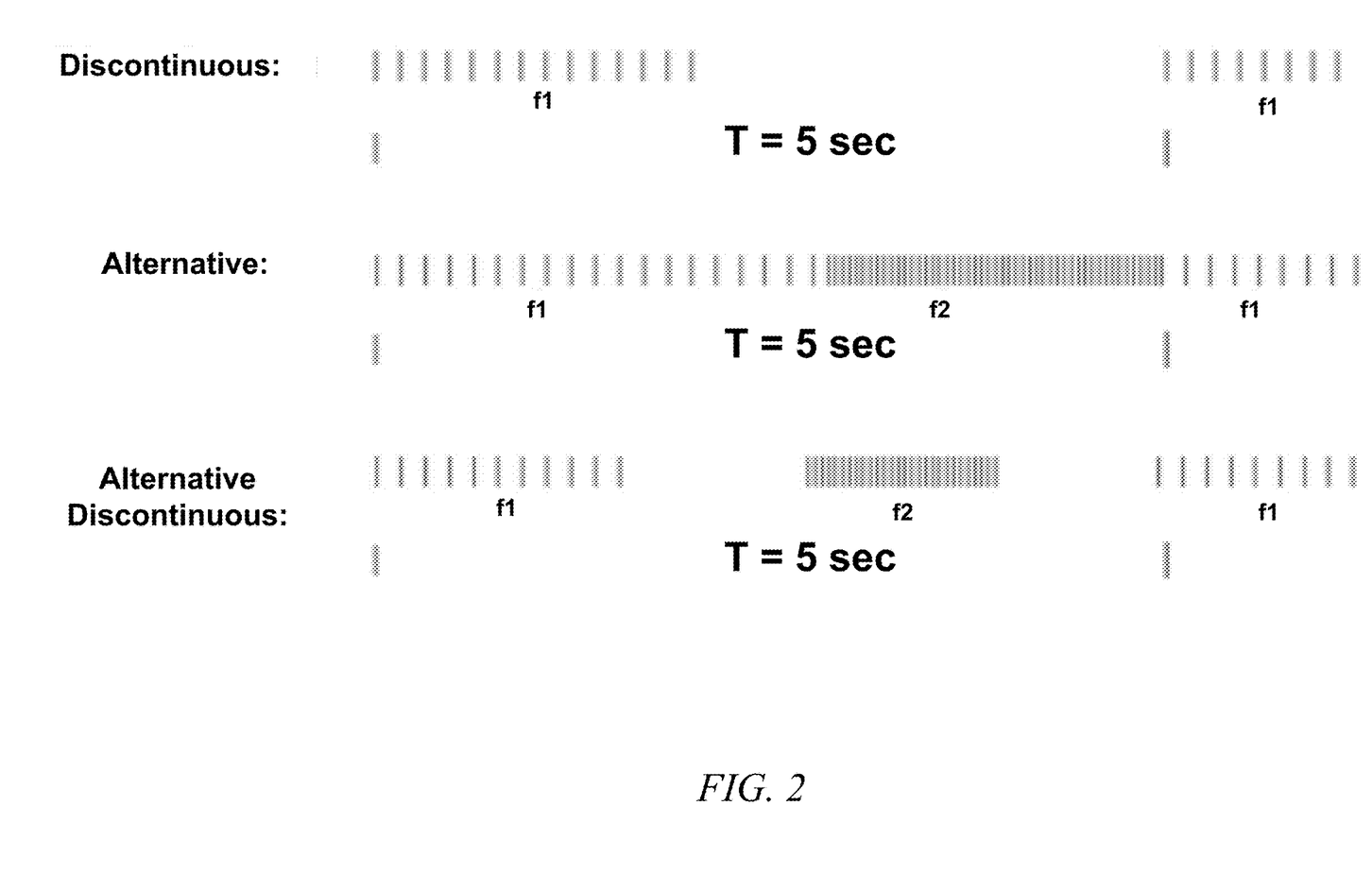
FIG. 2 illustrates high frequency stimulation modes in accordance with a conventional electro-acupuncture technique.

As another example, reference [2] describes additional modes in accordance with high frequency stimulation. These are illustrated in FIG. 2 and described as a discontinuous mode, which includes a train of pulses at frequency f1 (5 Hz) followed by a rest period, an alternative mode that includes two alternate trains of pulses with a frequency f1 (5 Hz) and f2 (120 Hz), and a discontinuous alternative mode that alternates between two frequencies f1 and f2, with a period of rest between pulse trains. The reference [2] implements the stimulation starting at relatively low levels (e.g., under a particular stimulation threshold) and increases progressively until the desired effects are obtained.

Although the aforementioned techniques may alleviate patient pain to some degree, some are not compatible for use during MRI scanning. Other current analgesic techniques have several drawbacks including, in the case of drugs, side-effects and the patient's loss of the ability to detect other sensations such as temperature. Moreover, current stimulation techniques can be invasive, and generally require the exact stimulation point to be known in advance such that the appropriate therapeutic stimulation can be applied as needed to alleviate pain in that region. As a result, additional improvements are needed to avoid PNS without significant drawbacks or associated risks.

Therefore, a goal of the embodiments as described herein is to overcome these drawbacks by transiently downgrading the perceived degree of severity (i.e., from tingling to twitching and subsequent painful sensations) using an analgesia means. The embodiments as described herein include implementing the analgesia means to facilitate a comfortable paraesthesia that only involves territories for which potentially painful PNS may occur. A further goal of the embodiments as described herein is to provide both temporal and spatial control of the target region affected by induced analgesic effects. Still further, a goal of the embodiments as described herein is to provide blocking of conduction of neural activity at the level of that region that would otherwise manifest PNS effects.

As further discussed herein, the embodiments implement a modulated stimulation using magnetic resonance gradient waveforms. In doing so, the aim is to provoke or stimulate a comfortable electrical-induced paraesthesia involving only the potential painful nerves and only for the duration of MR scanning. As a result, the embodiments discussed herein enable analgesia to be induced at a specific location associated with a particular nerve or group of nerves that are co-located where an initial stimulation due to strong switching MR gradients would occur.

In other words, by modulating the gradient waveforms themselves, any region prone to PNS is also exposed to electrical stimulation to counteract the PNS effect via delivery of electrically-induced analgesia at the same location. Thus, contrary to traditional or electric neural stimulation of acupuncture points, which requires an exact detection of the stimulation points to reach a regional induced analgesia where potential discomfort or pain occurs, the embodiments discussed herein facilitate inducing the analgesic effect at the area and respective nerves where potential severe discomfort or painful response would otherwise be induced by prior art gradient waveforms. The advantage is that a precise stimulation area does not need to be known in advance, which may be difficult considering that the body area subject to PNS stimulation changes with the patient position, coil geometry, gradient axis, nerve type, and nerve trajectory.

Figure 3:
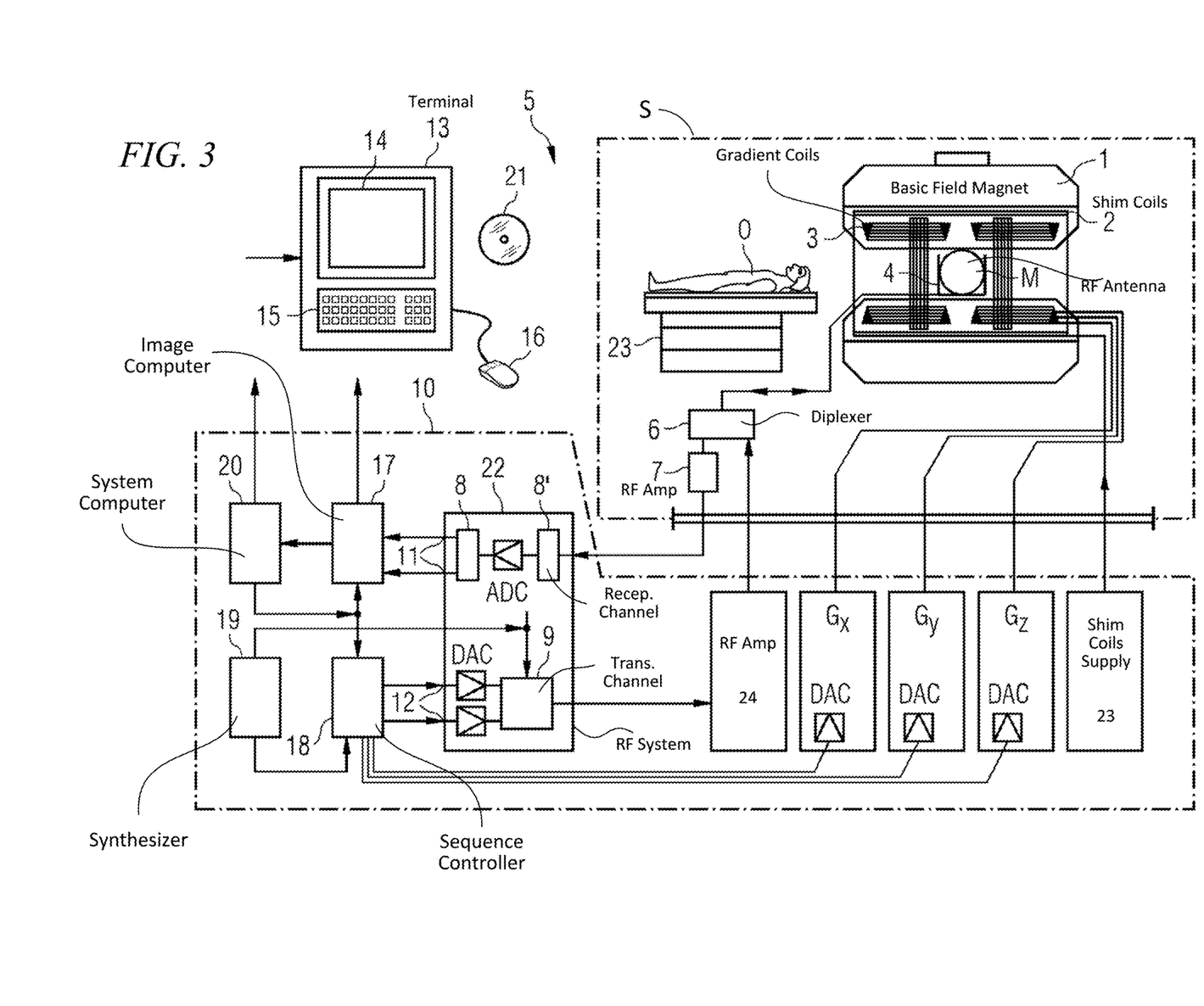
FIG. 3 illustrates a representation of a magnetic resonance device according to an exemplary embodiment.

FIG. 3 schematically illustrates a magnetic resonance apparatus 5 (e.g., a magnetic resonance imaging or tomography device). A basic field magnet 1 generates a temporally-constant strong magnetic field for the polarization or alignment of the nuclear spin in a region of an examination subject O, such as a portion of a human body that is to be examined, and who is lying on a table 23 to be moved into the magnetic resonance apparatus 5. The high degree of homogeneity in the basic magnetic field necessary for the magnetic resonance measurement (data acquisition) is defined in a typically sphere-shaped measurement volume M, in which the portion of the human body that is to be examined is placed. To support the homogeneity requirements, temporally-constant effects are eliminated by shim-plates made of ferromagnetic materials that are placed at appropriate positions. Temporally-variable effects are eliminated by shim-coils 2 and an appropriate control unit 23 for the shim-coils 2.

A cylindrically-shaped gradient coil system 3 (or alternatively, gradient field system) is incorporated in the basic field magnet 1, composed of three windings. Each winding is supplied by a corresponding amplifier Gx, Gy, and Gz, with power for generating a linear gradient field in a respective axis of a Cartesian coordinate system. The first partial winding of the gradient field system 3 generates a gradient Gx in the x-axis, the second partial winding generates a gradient Gy in the y-axis, and the third partial winding generates a gradient Gz in the z-axis. Each corresponding amplifier Gx, Gy and Gz has a digital-analog converter (DAC), controlled by a sequence controller 18 for the accurately-timed generation of gradient pulses.

A radio-frequency antenna 4 is located within the gradient field system 3, which converts the radio-frequency pulses provided by a radio-frequency power amplifier 24 into a magnetic alternating field for the excitation of the nuclei by tipping ("flipping") the spins in the subject or the region thereof to be examined, from the alignment produced by the basic magnetic field. The radio-frequency antenna 4 is composed of one or more RF transmitting coils and one or more RF receiving coils in the form of an annular, linear, or matrix type configuration of coils. The alternating field based on the precessing nuclear spin, i.e., the nuclear spin echo signal normally produced from a pulse sequence composed of one or more radio-frequency pulses and one or more gradient pulses, is also converted by the RF receiving coils of the radio-frequency antenna 4 into a voltage (measurement signal), which is transmitted to a radio-frequency system 22 via an amplifier 7 of a radio-frequency receiver channel 8, 8'.

The radio-frequency system 22 furthermore has a transmitting channel 9, in which the radio-frequency pulses for the excitation of the magnetic nuclear resonance are generated. For this purpose, the respective radio-frequency pulses are digitally depicted in the sequence controller 18 as a series of complex numbers, based on a given pulse sequence provided by the system computer 20. This number series is sent via an input 12, in each case, as real and imaginary number components to a digital-analog converter (DAC) in the radio-frequency system 22 and from there to the transmitting channel 9. The pulse sequences are modulated in the transmitting channel 9 to a radio-frequency carrier signal, the base frequency of which corresponds to the resonance frequency of the nuclear spin in the measurement volume. The modulated pulse sequences of the RF transmitter coil are transmitted to the radio-frequency antenna 4 via an amplifier 24.

Switching from transmitting to receiving operation occurs via a transmission-receiving switch 6. The RF transmitting coil of the radio-frequency antenna 4 radiates the radio-frequency pulse for the excitation of the nuclear spin in the measurement volume M and scans the resulting echo signals via the RF receiving coils. The corresponding magnetic resonance signals obtained thereby are demodulated to an intermediate frequency in a phase sensitive manner in a first demodulator 8' of the receiving channel of the radio-frequency system 22, and digitalized in an analog-digital converter (ADC). This signal is then demodulated to the base frequency. The demodulation to the base frequency and the separation into real and imaginary parts occurs after digitization in the spatial domain in a second demodulator 8, which emits the demodulated data via outputs 11 to an image processor 17.

In an image processor 17, an MR image is reconstructed from the measurement data obtained in this manner, which includes computation of at least one disturbance matrix and the inversion thereof, in the image processor 17. The management of the measurement data, the image data, and the control program occurs via the system computer 20. The sequence controller 18 controls the generation of the desired pulse sequences and the corresponding scanning of k-space with control programs. The sequence controller 18 controls accurately-timed switching (activation) of the gradients, the transmission of the radio-frequency pulse with a defined phase amplitude, and the reception of the magnetic resonance signals. The time base for the radio-frequency system 22 and the sequence controller 18 is provided by a synthesizer 19. The selection of appropriate control programs for the generation of an MR image, which are stored, for example, on a DVD 21, as well as other user inputs such as any suitable number N of adjacent clusters, which are to collectively cover the desired k-space, and the display of the generated MR images, occurs via a terminal 13, which includes units for enabling input entries, such as, e.g. a keyboard 15, and/or a mouse 16, and a unit for enabling a display, such as, e.g. a display screen.

The components within the dot-dash outline S are commonly called a magnetic resonance scanner, a magnetic resonance data acquisition scanner, or simply a scanner. The components within the dot-dash outline 10 are commonly called a control unit, a control device, or a control computer.

Thus, the magnetic resonance apparatus 5 as shown in FIG. 3 may include various components to facilitate the measurement, collection, and storage of MRI image data and/or MRI phase data. The embodiments described herein are directed to the specific manner in which the RF transmitting coil of the radio-frequency antenna 4 radiates the radio-frequency pulse for the excitation of the nuclear spin in the measurement volume M. Additionally, the embodiments described herein are directed the specific manner in which the gradient coil system 3 generates, via each respective amplifier Gx, Gy, and Gz, a linear gradient field in a respective axis of a Cartesian coordinate system.

In the case of the generation of the RF pulse, embodiments include the RF pulses being generated via the radio-frequency system 22 using the transmitting channel 9 based on a given pulse sequence provided by the system computer 20, as discussed above. Moreover, in the case of the generation of the linear gradient field via the respective amplifier Gx, Gy, and Gz, the linear gradient field may include components Gx, Gy, and Gz, which are depicted in accordance with their respective axis of the Cartesian coordinate system. Furthermore, the gradient field components Gx, Gy, and Gz may be generated in accordance with the embodiments as described herein via the gradient amplifiers Gx, Gy, and Gz in conjunction with the sequence controller 18 and synthesizer 19, as described above. The gradient field components Gx, Gy, and Gz may thus be generated as described herein in accordance with a desired pattern, sequence, timing, etc., as identified via the control computer 20, as discussed above.

Figure 4:
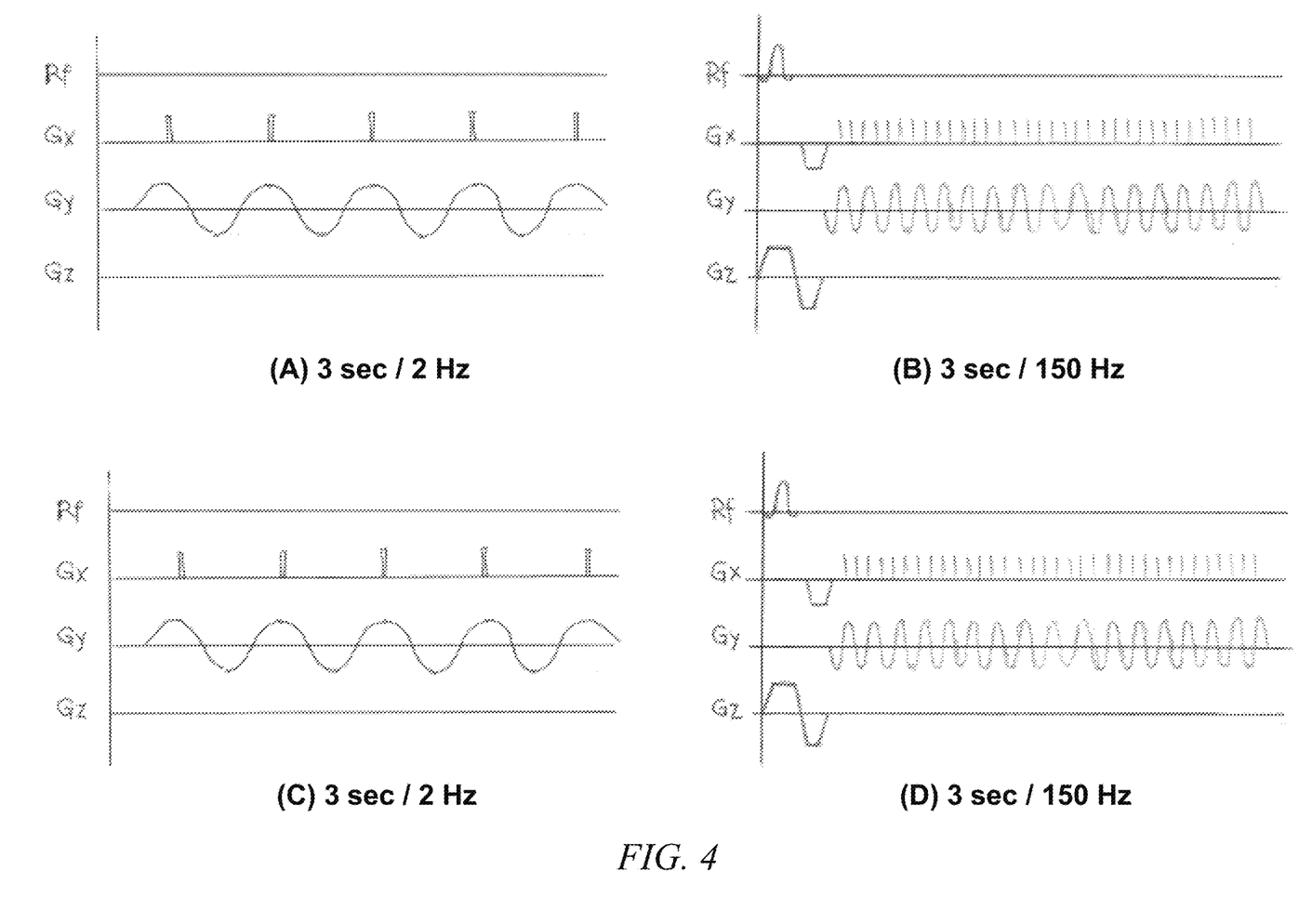
FIG. 4 illustrates an example of switching gradient frequencies during an MR sequence to block patient pain transmission channels according to an exemplary embodiment.

FIG. 4 illustrates an example of switching gradient frequencies during an MR sequence to block patient pain transmission channels according to an exemplary embodiment. Referring back to FIG. 3, the example gradient amplitude values shown throughout FIGS. 4A-4D, as well as FIGS. 5 and 6, denote field values within the imaging volume M of the scanner to which a patient's body would be directly exposed.

One example of mixed gradient switching is shown in FIG. 4, in which two different gradient switching frequencies are implemented, one being a low frequency (e.g., 2 Hz as shown) that is switched with a high frequency (e.g., 150 Hz as shown). In particular, each of the plots A-D as shown in FIG. 4 is associated with a three-second window and represents an example of the time-varying amplitude of the gradient field components Gx, Gy, and Gz, as well as the RF pulse. In other words, the plots A-D represent changes in the amplitude of the RF pulse and gradient field components over time in a sequential manner, starting with plot A and ending with plot D (i.e., A-B-C-D). In this case, the plots A-D represent the changes in the amplitude of the RF pulse and gradient field components for an example 12-second duration while an MR scan is performed, for example, via the magnetic resonance apparatus 5 as shown in FIG. 3.

The plots A-D as shown in FIG. 4 are for purposes of brevity, and the switching as shown in FIG. 4 may include any suitable number of time windows, each having any suitable respective time duration, and need not be equal to one another. The amplitude of the RF pulse and gradient field components are not labeled in FIG. 4 for brevity. However, the embodiments described herein include the amplitude or intensity of these components being any suitable intensity level to provide suitable MR imaging results and to achieve suitable blockage of pain transmission paths as discussed herein. Moreover, the specific frequencies as shown in FIG. 4 are by way of example and not limitation. For example, one or more of the gradient field components Gx, Gy, and Gz may have a lower frequency in the range of 1-5 Hz (or a wider frequency range), and a higher frequency in the range of 80-200 Hz (or a wider frequency range).

Thus, in various embodiments, the amplitude and/or the slew-rate of the gradient pulses are higher than the limits imposed in accordance with their conventional usage in MR scanners to avoid the aforementioned PNS effects. Some examples of the increases in the amplitude and/or slew rate over conventional gradient pulses may be 20%, 30%, 40%, 50%, or even higher. Furthermore, embodiments also include maintaining the amplitudes of the gradient pulses below than three times the limits of conventional gradient pulse usage art to avoid respiratory and cardiac stimulation, as noted above.

In any event, the embodiments described herein may include the time-varying amplitude of the gradient field components Gx, Gy, and Gz having any suitable frequency, and may be time-varied independently from one window to the next subsequent window. For instance, the profile of the gradient field components Gx, Gy, and Gz (i.e., in terms of frequency and amplitude) are identical in plots A and C, and likewise identical in plots B and D, as shown in FIG. 4. This need not be the case, however, and the gradient field components Gx, Gy, and Gz may be varied in accordance with any suitable pattern such that the amplitude and/or frequencies of the gradient field components Gx, Gy, and Gz follow any suitable deviation from one time window and the next, and may or may not repeat within a suitable duration of time.

Again, in various embodiment, the gradient field components Gx, Gy, and Gz may be switched to block the pain transmission channels for at least the time of running the MR imaging procedure. Further in accordance with such embodiments, one of the two gradient field component frequencies may facilitate signal encoding (e.g., an EPI readout), whereas the second gradient field component frequency may be selected such that the presence of this gradient field component has no (or negligible, i.e., less than a threshold value of contribution) effect on spins. This frequency is referred to herein as a "dark-mode frequency," as depicted as the 2 Hz frequency shown in plots A and C of FIG. 4. As further discussed herein, the embodiments include several techniques regarding when the dark-mode pulses (i.e., pulses in accordance with the dark-mode frequency) are introduced within a periodic MRI scanning sequence.

In other words, the gradient pulse sequences as depicted in FIGS. 4A and 4C (i.e., not the RF pulse) are dark-mode sequences used only for nerve stimulation, and generally do not otherwise provide a valuable contribution to the imaging process. Again, the dark-mode sequences as shown in FIGS. 4A and 4C may have a different, lower frequency than the gradient pulses as shown in FIGS. 4B and 4D, which are used for performing the imaging sequence. However, other gradient pulse parameters associated with the gradient pulses shown in each of 4A-4D (e.g., the amplitude, slew-rate, and pulse shape) are the same as one another (e.g., identical or within a certain threshold tolerance such as 1%, 5%, etc.).

Again, the embodiments described herein may include varying the frequency and/or amplitude of one or more of the gradient field components Gx, Gy, and Gz from one time period to another (e.g., the time "windows" as shown in each of plots A-D in FIG. 4 above). FIG. 4 illustrates an embodiment in which the frequency of the gradient field components Gx and Gy are switched between different frequencies (e.g., 2 Hz and 150 Hz) to induce electrostimulation for blockage of pain transmission channels. Other embodiments, however, include the use of a single frequency for the gradient field components Gx, Gy, and Gz but varying the amplitude over time for the duration of an MR scan, as discussed below with reference to FIG. 5. Still further, other embodiments include inserting pulses to achieve nerve conduction blockage while shaping the inserted pulses in a manner that does not influence the image contrast, as discussed further below with respect to FIGS. 6A-B.

Figure 5:
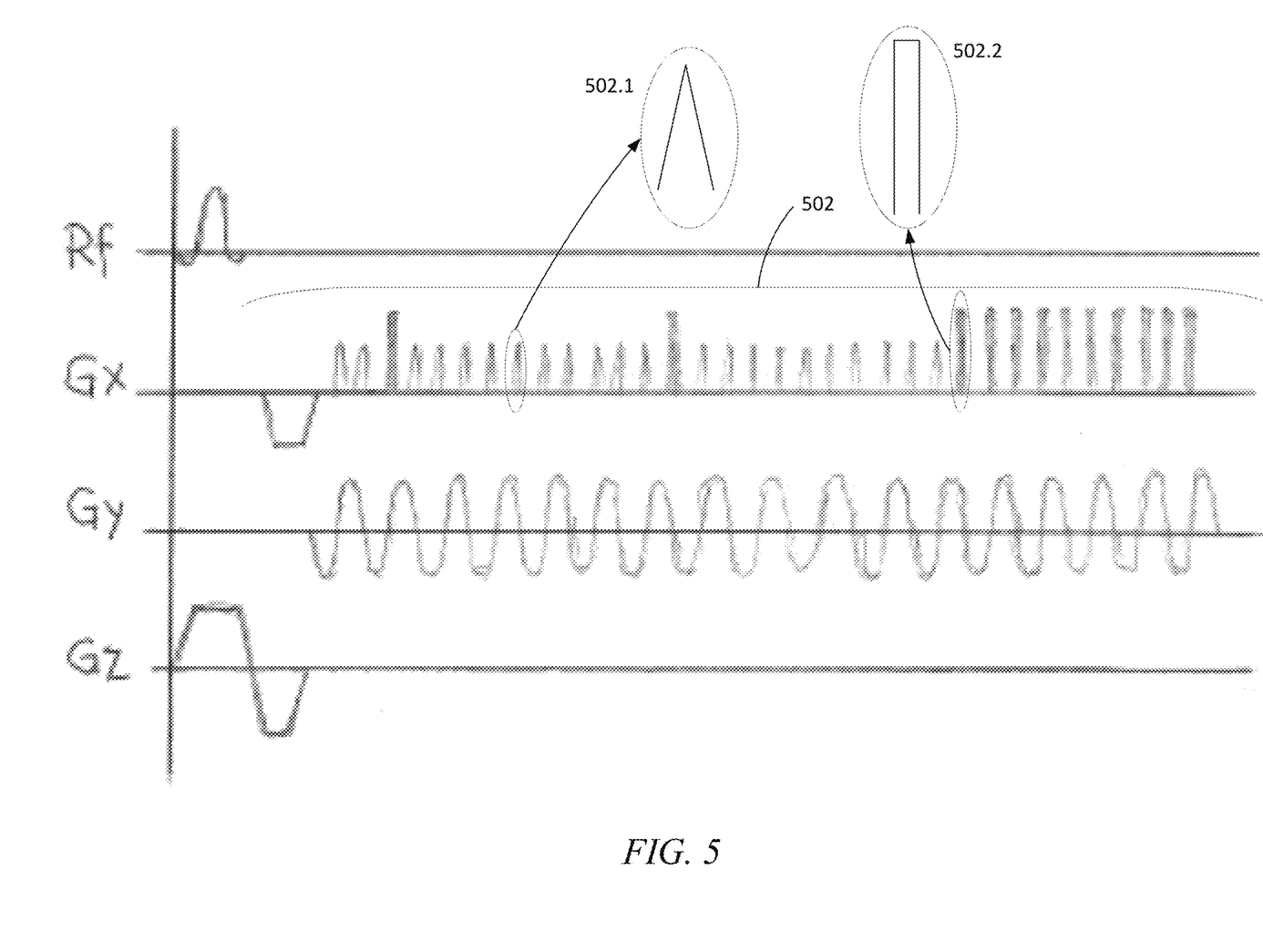
FIG. 5 illustrates another example of varying gradient pulse amplitude during an MR sequence to block patient pain transmission channels according to an exemplary embodiment.

The embodiments described herein with reference to FIGS. 5 and 6 may be implemented based upon the frequencies used for traditional kilohertz electrical stimulation (KES) techniques as discussed above. Again, various techniques exist for blocking conduction of neural activity including application of pressure, temperature, and pharmacological agents. However, these methods do not provide temporal or spatial control in terms of time of onset or offset and the tissue region affected. KES, on the other hand, provides both temporal and spatial control of the target tissue affected. Clinically, KES is currently used in spinal cord stimulation for the treatment of chronic pain without paresthesia, abdominal vagus nerve stimulation for modulation of satiety and appetite, as well as somatic nerve stimulation therapies for treatment of post-amputee pain.

Previous studies have demonstrated that frequencies greater than 5 kHz are required to achieve a true nerve conduction block. Frequencies as high as 70 kHz have been used experimentally, while frequencies up to 100 kHz have been evaluated in computational studies. The embodiments described herein with respect to FIGS. 5 and 6 leverage KES techniques by using the gradient field components Gx, Gy, and Gz, and/or introducing dark-mode gradient pulses as delivery mechanisms to cause induced electrical stimulation. In doing so, the embodiments described herein achieve the desired KES results.

In other words, contrary to conventional KES techniques, which reply upon the application of stimulating kHz electric pulses via surface or implanted electrodes, the embodiments as described herein function to block nerve conduction by the stimulating effect caused by pulsing MR gradients. However, depending upon the particular MR sequence that is used, the embodiments described herein implement two different techniques to facilitate the target stimulation frequency independent of the current sequence timing. This target stimulation frequency may be any suitable range of frequencies that achieves the desired result of nerve conduction blocking, such as those described herein with reference to KES techniques (e.g., 5 kHz-100 kHz, 5 kHz-125 kHz, 5 kHz-150 kHz, etc.). Moreover, the specific target stimulation frequency for a given MR sequence may be further refined over time as additional experimental data or other suitable feedback is received, which may be based upon the particular type of MR scan, the size and/or age of the patient, a targeted region of the MR scan, etc. The target frequency may be calculated or otherwise determined via one or more components of the MR apparatus 5 as shown in FIG. 3 (e.g., the control computer 20).

In particular, and as described in further detail with reference to FIG. 5, if the frequency of the gradient pulses in accordance with the timing of the current MR sequence is higher than a required target stimulation frequency, then only some of the gradient pulses may be modified to induce a stronger nerve block stimulation. For example, as shown in FIG. 5, during an MR scan a combination of gradient pulse amplitudes are introduced for the PNS inducing gradient axis, which are the amplitudes of the gradient pulses 502 associated with the gradient field component Gx in this example. Thus, embodiments include modifying one or more of the amplitudes of the gradient pulses 502 such that some of the Gx pulses stimulate stronger than others.

As shown in FIG. 5, embodiments include implementing a KES effect by periodically introducing some of the gradient pulses 502 having a higher amplitude than others, which can be observed via the detail shown with respect to the two example Gx gradient pulses 502.1 and 502.2. Additionally or alternatively, embodiments also include implementing the KES effect by periodically introducing some of the Gx gradient pulses with a faster switching time than others (e.g., the Gx gradient pulse 502.2 has a faster switching time than the Gx gradient pulse 502.1). In any event, the embodiments described herein include maintaining an equal area below the pulse envelope for each of the Gx gradient pulses (or another appropriate gradient field component, as the case may be) to realize identical spin encoding momentums.

However, if the frequency of the gradient pulses in accordance with the timing of the MR sequence is lower than the required target stimulation frequency, embodiments include inserting additional gradient pulses between the sequence pulses. Although these additional pulses are not shown in FIG. 5 for purposes of brevity, such additional pulses may be shaped such that the image contrast remains unchanged, which may be achieved using, for example, fast switching bipolar pulses or "dark-mode" pulses. Again, in accordance with the embodiments described herein, the term "dark-mode" with respect to a gradient pulse is a nerve-stimulating pulse that has no impact or an insignificant impact (i.e., less than a threshold value of contribution) on a resulting image contrast associated with an MR scan. For instance, a dark-mode gradient pulse may be any suitable gradient pulse that is applied after a previous k-space acquisition (i.e., after the readout period) and prior to the next RF excitation within a periodic MRI measuring sequence.

To provide another example, dark-mode gradient pulses may include the re-use of any (or only some of) the already-available dephaser gradient pulses within a certain imaging sequence. These may include, for example, the dephasers used around the 180° inversion RF-pulses. These may also include, for instance, the gradient pulses used as spoilers to eliminate residual magnetization at the end of any periodic MRI sequence.

To provide yet another example of an implementation of dark-mode gradient pulses, the dark-mode gradient pulses may be formed as any suitable waveform that starts and ends at the same location within k-space where the pulse originally began. This is one example of a bipolar gradient pulse with zero integral momentum (i.e., the area under the pulse waveform). In shaping a gradient pulse in this manner, embodiments facilitate the amplitude and the slew-rate of the positive, negative, or both the positive and the negative half-waves producing nerve stimulation.

Figure 6A:
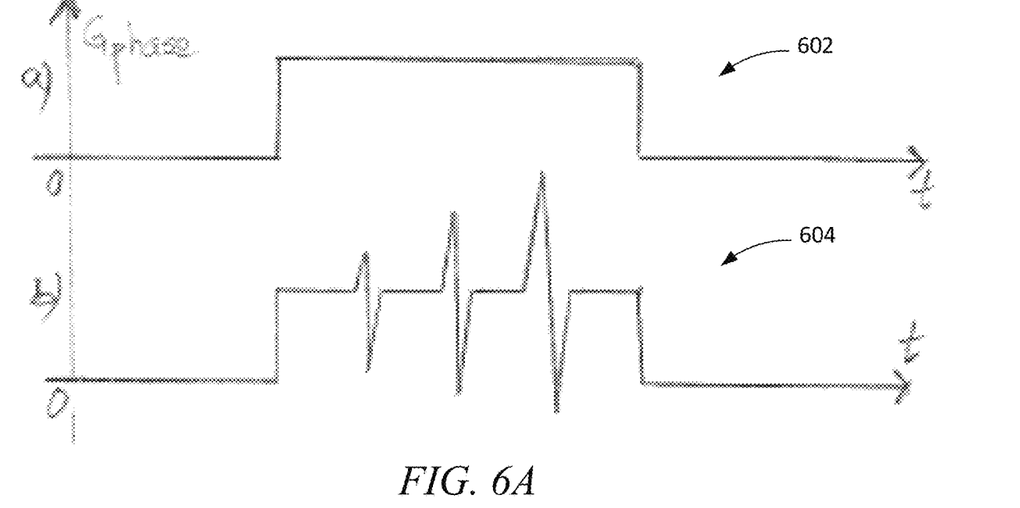
FIG. 6A illustrates an example of superimposing high-amplitude and fast-gradient pulses onto conventional phase-encoded gradient pulses during phase encoding to generate dark-mode gradient pulses during an MR sequence to block patient pain transmission channels according to an exemplary embodiment.

Yet another example of an implementation of dark-mode gradient pulses includes high-amplitude and fast-gradient pulses superimposed over conventionally phase-encoded gradient pulses that are applied during phase encoding, which is shown in FIG. 6A as a dark-mode gradient pulse 604. Such embodiments recognize that, advantageously, during phase-encoding the gradient pulse waveform (i.e., the pulse shape) is unimportant, as the integral momentum is key to realize identical spin encoding momentums. Thus, by conserving the integral momentum, multiple stimulating pulses can be superimposed during the phase encoding part of a MR sequence.

For instance, FIG. 6A depicts a conventional phase-encoding gradient pulse 602 used during MRI sequences. The embodiments as described herein include superimposing onto this phase-encoding gradient pulse 602 embedded nerve stimulation via the introduction of high-amplitude and fast-gradient pulses, as shown in FIG. 6A, to generate the dark-mode gradient pulse 604. The area below the pulse envelope is same for both the conventional phase-encoding gradient pulse 602 and the dark-mode gradient pulse 604. In this way, identical spin encoding momentums are realized in each case.

Figure 6B:
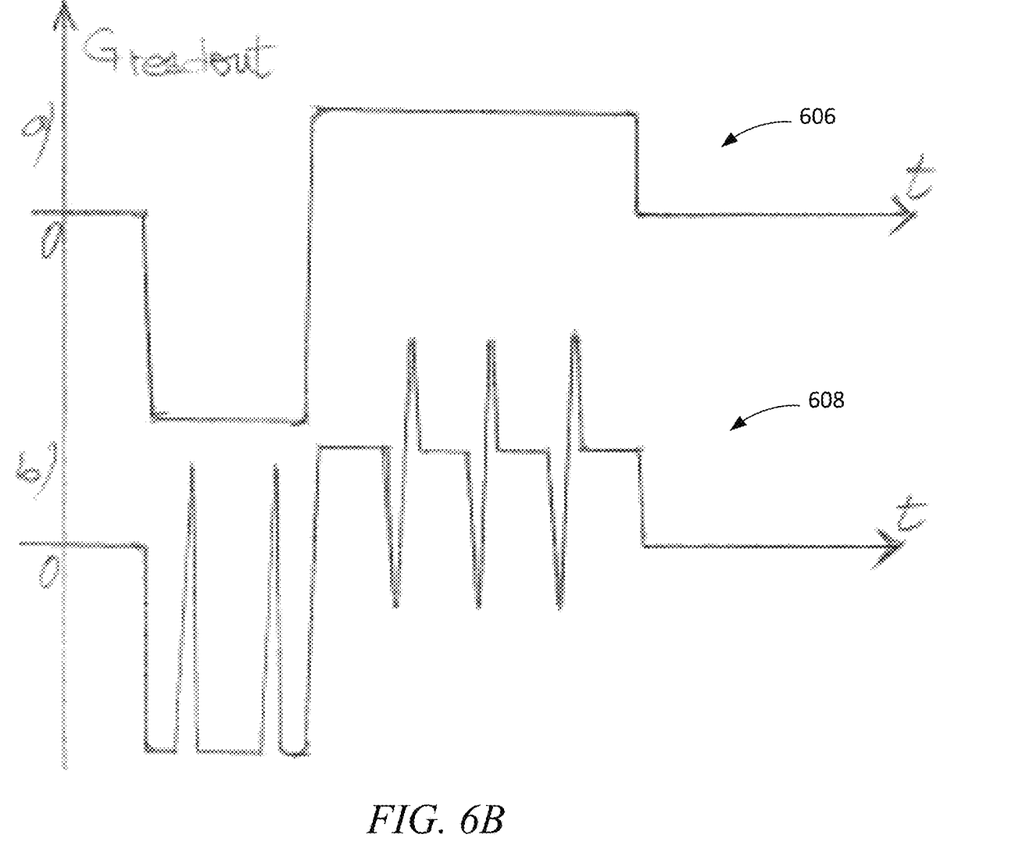
FIG. 6B illustrates an example of superimposing high-amplitude and fast-gradient pulses onto conventional readout gradient pulses during frequency encoding to generate dark-mode gradient pulses during an MR sequence to block patient pain transmission channels according to an exemplary embodiment.

Another example of an implementation of dark-mode gradient pulses includes high-amplitude and fast-gradient pulses superimposed over conventional readout pulses that are applied during frequency encoding, which is shown in FIG. 6B as a dark-mode readout pulse 608. For instance, FIG. 6B depicts a conventional readout gradient pulse 606 used during the readout phase of MRI sequences. The embodiments as described herein include superimposing onto this conventional readout gradient pulse 606 embedded nerve stimulation via the introduction of high-amplitude and fast-gradient pulses, as shown in FIG. 6B, to generate the dark-mode readout gradient pulse 608.

As a result, the area below the negative pulse envelope associated with the conventional readout gradient pulse 606 is the same as that of the dark-mode readout gradient pulse 608. In this way, identical spin encoding momentums are realized in each case. The positive pulse modifies the readout trajectory in k-space, however, which needs to be considered during image reconstruction. That is, during the readout period, the resulting trajectory throughout the k-space is important and it needs to be pre-calibrated and considered in the image reconstruction. Fortunately, image reconstruction methods for arbitrary, non-Cartesian k-space trajectories (e.g. spiral, radial, phyllotaxis, etc.) are well known, and embodiments include the application of such techniques when conventional readout gradient pulses are modified in this manner.

Again, the embodiments described herein are by way of example and not limitation. The various embodiments described herein may be further modified by a person skilled in the art without departing from the spirit and scope of the disclosure. For instance, the various gradient pulses and/or dark mode pulses may be defined in accordance with any suitable number of time-varying parameters, i.e., parameters that are varied during a particular portion of an MRI scan such as during an MR sequence, during phase encoding, during frequency encoding, etc.

As noted herein, there are other alternative embodiments to generate the dark-mode gradient pulses, and those disclosed herein are by way of example and not limitation. For example, the gradient pulses and/or dark-mode gradient pulses may be defined in accordance with time-varying parameters including frequency, slew rate, switching time, amplitude, waveform shape, rise time, fall time, superimposed pulses, the insertion of dark-mode pulses, etc. Thus, during an MR scan, one or more of these time-varying parameters may be adjusted at any time, in any combination, and for any duration of time (e.g., different combinations of sequential windows using different gradient pulse frequencies) to achieve the desired electrically-induced stimulation results (e.g., pain transmission path blocking).

Referring back to FIG. 3, the magnetic resonance apparatus 5 may include additional, fewer, or alternate components that are not depicted in FIG. 3 for purposes of brevity. For instance, the magnetic resonance apparatus 5 may alternatively include, or include in addition to the DVD 21, one or more non-transitory computer-readable data storage mediums in accordance with various embodiments of the present disclosure. Thus, the aforementioned non-transitory computer-readable media may be loaded, stored, accessed, retrieved, etc., via one or more components accessible to, integrated with, and/or in communication with the magnetic resonance apparatus 5 (e.g., network storage, external memory, etc.). For example, such data-storage mediums and associated program code may be integrated and/or accessed via the terminal 13, the control device 10 or components thereof such as the control computer 20, the image computer 17, the sequence controller 18, the RF system 22, etc.

The executable program code, which may be executed via one or more components of the magnetic resonance apparatus 5 to perform the techniques as discussed herein, may facilitate the performance of computer-implemented methods in this manner in accordance with the embodiments described herein.

Furthermore, any portions of the embodiments described herein may be executed manually, semi-autonomously, or fully autonomously. To provide an illustrative example of the overall operation of the embodiments as described herein, one or more components of or associated with the magnetic resonance apparatus 5 performing the MR sequences as discussed herein may generate one or more control signals (or receive one or more control signals from other portions of the magnetic resonance apparatus 5) that result in the execution of various operations. These operations may include, for instance, generation of the various gradient pulses as disused herein.

In various embodiments, one or more processors associated with the magnetic resonance apparatus 5 (e.g., the terminal 13, the control device 10 or components of the control device 10 such as the system computer 20, the image computer 17, the sequence controller 18, the RF system 22, etc.) as described herein may likewise generate one or more control signals in response to user input, in response to the execution of computer-readable instructions. The control signals generated in this manner may thus result in the magnetic resonance apparatus 5 (or one or more components thereof) performing the various gradient pulse generation techniques as described herein. The various computing acts performed by the magnetic resonance apparatus 5 (or one or more components thereof) may be in response to any combination of user input and/or control signals that are automatically generated in response to the occurrence of certain events, e.g., upon the initiation of an MR sequence, upon the generation of MRI setting parameters, upon the initiation of the phase-encoding phase during an MRI scan, upon the initiation of the frequency-encoding portion of an MRI scan, etc.

Although the present disclosure has been illustrated and described in detail with the preferred exemplary embodiments, the disclosure is not restricted by the examples given, and other variations can be derived therefrom by a person skilled in the art without departing from the protective scope of the disclosure. Although modifications and changes may be suggested by those skilled in the art, it is the intention to embody all changes and modifications as reasonably and properly come within the scope of their contribution to the art.

It is also pointed out for the sake of completeness that the use of the indefinite articles "a" or "an" does not exclude the possibility that the features in question may also be present more than once. Similarly, the term "unit" does not rule out the possibility that the same consists of a plurality of components which, where necessary, may also be distributed in space.

The claims described herein and the following description in each case contain additional advantages and developments of the embodiments as described herein. In various embodiments, the claims of one claims category can, at the same time, be developed analogously to the claims of a different claims category and the parts of the description pertaining thereto. Furthermore, the various features of different exemplary embodiments and claims may also be combined to create new exemplary embodiments without departing from the spirit and scope of the disclosure.

REFERENCES

The following references are cited throughout this disclosure as applicable to provide additional clarity, particularly with regards to terminology. These citations are made by way of example and ease of explanation and not by way of limitation.

Citations to the following references are made throughout the application using a matching bracketed number, e.g., [1].
[1] Chinese Patent Application No. CN101069769A.
[2] G. Gh. Litarczek, et al.: "Research in electro-acupuncture anaesthesia," in: 1st International Conference on Advancements of Medicine and Health Care through Technology, MediTech2007, 27-29 Sep. 2007, Cluj-Napoca, ROMANIA.

What is claimed is:
1. A magnetic resonance (MR) apparatus for inducing electrical stimulation to inhibit pain perceived by a patient caused by peripheral nerve stimulation (PNS) during a magnetic resonance scan, comprising:

a magnetic resonance data acquisition scanner comprising a gradient coil system including a plurality of coil windings; and
a plurality of gradient amplifiers, each one of the plurality of gradient amplifiers being coupled to a sequence controller and to a respective one of the plurality of coil windings,
wherein the sequence controller is configured to control each respective one of the plurality of gradient amplifiers to cause one or more of the plurality of coil windings to (i) respectively generate timed gradient pulses, and (ii) when it is determined via a control computer associated with the MR apparatus that the frequency of the one or more of the timed gradient pulses in accordance with the timing of an MR sequence is less than a predetermined frequency, to generate one or more dark-mode gradient pulses that are inserted between the one or more of the timed gradient pulses, and
wherein one or more of the timed gradient pulses are generated with one or more time-varying parameters such that, when the patient is exposed to the one or more of the timed gradient pulses and/or the one or more dark-mode gradient pulses, electrical stimulation is induced in at least one region of the patient resulting in an electrically-induced analgesia at the at least one region of the patient during the MR scan.

2. The MR apparatus of claim 1, wherein:
the one or more of the timed gradient pulses are generated during an MR sequence within a plurality of successive time windows, and
the time-varying parameters include a frequency of the one or more of the timed gradient pulses such that the one or more of the timed gradient pulses are generated having a first frequency within a first time window from among the plurality of successive time windows and a second frequency within a second time window from among the plurality of successive time windows.

3. The MR apparatus of claim 2, wherein the first time window and the second time window are chronologically-adjacent, and
wherein the first frequency is different than the second frequency.

4. The MR apparatus of claim 3, wherein the first frequency is within a range of 1 Hz-5 Hz, and
wherein the second frequency is within a range of 1 Hz-150 Hz.

5. The MR apparatus of claim 1, wherein the time-varying parameters include an amplitude and/or a switching time of the one or more of the timed gradient pulses such that, within a time window during the MR scan, a first portion of the one or more of the timed gradient pulses has a different amplitude and shape than a second portion of the one or more of the timed gradient pulses.

6. The MR apparatus of claim 5, wherein each of the one or more of the timed gradient pulses within the time window during the MR scan have an equal area below each respective pulse envelope.

7. The MR apparatus of claim 5, wherein the first portion of the one or more of the timed gradient pulses are generated having a different amplitude and shape than the second portion of the one or more timed gradient pulses within the time window during the MR scan in response to a determination, via a control computer, that the frequency of the one or more of the timed gradient pulses in accordance with the timing of an MR sequence is greater than a predetermined frequency.

8. The MR apparatus of claim 1, wherein the time-varying parameters include superimposing one or more pulses over a phase-encoding gradient pulse that is applied during phase encoding, the one or more superimposed pulses having a different amplitude and frequency than the phase-encoding gradient pulse to generate the one or more dark-mode gradient pulses, and
wherein an area below a pulse envelope associated with each respective one of the one or more dark-mode gradient pulses is equal to an area below a pulse envelope associated with a respective phase-encoding gradient pulse.

9. The MR apparatus of claim 1, wherein the time-varying parameters include superimposing one or more pulses over a readout gradient pulse that is applied during frequency encoding, the one or more superimposed pulses having a different amplitude and frequency than the readout gradient pulse to generate the one or more dark-mode gradient pulses, and
wherein an area below a pulse envelope associated with each respective one of the one or more dark-mode gradient pulses is equal to an area below a pulse envelope associated with a respective readout gradient pulse.

10. A non-transitory computer readable medium loaded onto a control computer of a magnetic resonance (MR) data acquisition scanner for inducing electrical stimulation to inhibit pain perceived by a patient caused by peripheral nerve stimulation (PNS) during a MR scan, the non-transitory computer readable medium having instructions stored thereon that, when executed by the control computer, cause the MR data acquisition scanner to:
control a sequence controller that is coupled to each one of a plurality of gradient amplifiers, each one of a plurality of gradient amplifiers being further coupled to a respective one of the plurality of coil windings of a gradient coil system,
wherein control of the sequence controller causes each respective one of the plurality of gradient amplifiers to cause one or more of the plurality of coil windings to (i) respectively generate timed gradient pulses, and (ii) when it is determined via a control computer associated with the MR apparatus that the frequency of the one or more of the timed gradient pulses in accordance with the timing of an MR sequence is less than a predetermined frequency, to generate one or more dark-mode gradient pulses that are inserted between the one or more of the timed gradient pulses, and
wherein one or more of the timed gradient pulses are generated with one or more time-varying parameters such that, when the patient is exposed to the one or more of the timed gradient pulses and/or the one or more dark-mode gradient pulses, electrical stimulation is induced in at least one region of the patient resulting in an electrically-induced analgesia at the at least one region of the patient during the MR scan.

11. The non-transitory computer readable medium as claimed in claim 10, wherein:
the one or more of the timed gradient pulses are generated during an MR sequence within a plurality of successive time windows, and
the time-varying parameters include a frequency of the one or more of the timed gradient pulses such that the one or more of the timed gradient pulses are generated having a first frequency within a first time window from among the plurality of successive time windows and a second frequency within a second time window from among the plurality of successive time windows.

12. The non-transitory computer readable medium as claimed in claim 11, wherein the first time window and the second time window are chronologically-adjacent, and
wherein the first frequency is different than the second frequency.

13. The non-transitory computer readable medium as claimed in claim 12, wherein the first frequency is within a range of 1 Hz-5 Hz, and
wherein the second frequency is within a range of 1 Hz-150 Hz.

14. The non-transitory computer readable medium as claimed in claim 10, wherein the time-varying parameters include an amplitude and/or a switching time of the one or more of the timed gradient pulses such that, within a time window during the MR scan, a first portion of the one or more of the timed gradient pulses has a different amplitude and shape than a second portion of the one or more of the timed gradient pulses.

15. The non-transitory computer readable medium as claimed in claim 14, wherein each of the one or more of the timed gradient pulses within the time window during the MR scan have an equal area below each respective pulse envelope.

16. The non-transitory computer readable medium as claimed in claim 14, further including instructions that, when executed by the control computer, cause the first portion of the one or more of the timed gradient pulses to be generated having a different amplitude and shape than the second portion of the one or more of the timed gradient pulses within the time window during the MR scan in response to a determination, via the control computer, that the frequency of the one or more of the timed gradient pulses in accordance with the timing of an MR sequence is greater than a predetermined frequency.

17. The non-transitory computer readable medium as claimed in claim 10, wherein the time-varying parameters include superimposing one or more pulses over a phase-encoding gradient pulse that is applied during phase encoding, the one or more superimposed pulses having a different amplitude and frequency than the phase-encoding gradient pulse to generate the one or more dark-mode gradient pulse, and
wherein an area below a pulse envelope associated with each respective one of the one or more dark-mode gradient pulses is equal to an area below a pulse envelope associated with a respective phase-encoding gradient pulse.

18. The non-transitory computer readable medium as claimed in claim 10, wherein the time-varying parameters include superimposing one or more pulses over a readout gradient pulse that is applied during frequency encoding, the one or more superimposed pulses having a different amplitude and frequency than the readout gradient pulse to generate the one or more dark-mode gradient pulse, and
wherein an area below a pulse envelope associated with each respective one of the one or more dark-mode gradient pulses is equal to an area below a pulse envelope associated with a respective readout gradient pulse.

* * * * *